United States Patent [19]

Lemley et al.

[11] Patent Number: 5,626,844

[45] Date of Patent: May 6, 1997

[54] MONOCLONAL ANTIBODY AGAINST RICIN A CHAIN

[75] Inventors: Paul V. Lemley, Gettysburg, Pa.; D. Craig Wright, Gaithersburg, Md.

[73] Assignee: The United States of America as represented by the Secretary of the Army, Washington, D.C.

[21] Appl. No.: 363,204

[22] Filed: Dec. 27, 1994

Related U.S. Application Data

[63] Continuation-in-part of Ser. No. 787,352, Nov. 4, 1991, abandoned.

[51] Int. Cl.⁶ .................. A61K 39/395; C07K 16/16; A61M 5/20
[52] U.S. Cl. .................. 424/141.1; 424/130.1; 530/387.1; 530/388.1; 530/388.5; 604/171
[58] Field of Search ............... 530/387.1, 388.1, 530/388.4, 388.5; 424/130.1, 141.1, 172.1; 604/171

[56] References Cited

PUBLICATIONS

Houston [J. Toxicol Clin. Toxicol. 19(4):385–389 (1982)].
Waldmann [Science 252:1657–1662 (1991)].
Harris et al. [TIBTECH 11:42–44 (1993)].
Youle et al. [JBC 262(10):4676–4682 (1987)].
Foxwell et al. [Toxicology 34(1):79–88 (1985)].

*Primary Examiner*—Donald E. Adams
*Attorney, Agent, or Firm*—John Francis Moran

[57] ABSTRACT

Monoclonal antibodies against the A chain of ricin have been found to be effective in protecting mammals from morbidity arising from exposure to ricin toxin. The neutralizing action of the antibodies does not appear to be mediated by complement or by immunoprecipitation. The antibodies of the invention are characterized as of isotype IgG1 having the binding characteristics which include: a) binding specifically to the neutralizing epitope of the ricin A chain and b) providing in vitro protection of at least 95% of EL-4 cells from 100 ng/mL ricin challenge when said antibody is present in the tissue culture at a level of at least 1000 ng/mL.

10 Claims, No Drawings

MONOCLONAL ANTIBODY AGAINST RICIN A CHAIN

This application is a continuation-in-part of U.S. Ser. No. 07/787,352 filed Nov. 4, 1991, now abandoned.

FIELD OF THE INVENTION

This invention relates to monoclonal antibodies which bind to the ricin A chain and which are not cross-reactive with ricin B chain. The monoclonal antibodies of the invention neutralize the toxicity of ricin and may be used to provide passive immunity to mammals susceptible to morbidity caused by exposure to ricin.

BACKGROUND OF THE INVENTION

Ricin is a very toxic protein obtained from the castor bean seeds. Ricin is a glycoprotein with a molecular weight of about 64–65 kD composed of an A chain having a weight of about 31 kD and a B chain having a molecular weight of about 33 kD. The A chain functions to inactivate ribosomes and inhibit protein synthesis of cells.

Each of the toxin's two subunits has a distinct role in toxicity. The B chain selectively binds to residual groups of galactose on the membrane surfaces of eukaryotic cells. The toxin is able to access the cytosol. It has been postulated that the toxin can enter the cytosol from an intracellular compartment not accessible to extracellular antibodies (Sandvig, et al ((*J. Biol. Chem.* 257, 7504–7513 (1982)).

The study of the ricin B subunit in translocation of the ricin into the cytosol has been studied fairly extensively. It has been proposed that intracellular galactose receptors mediate the effect of the ricin B. Antibodies to the ricin B chain have been shown to protect against the pathological effects of ricin toxin. U.S. Pat. No. 4,520,011 to Neville, et al. discloses and claims a method of inhibiting protein synthesis in target cells by addition of excess ricin B to compositions containing ricin A chain attached to antibodies that target particular cells. By adding an excess of ricin B chain it was possible to increase the effect of the targeting antibody/ricin A complex on the target cells. This increase in effect on target cells was attributed to the effect of ricin B in facilitating entry of ricin A into the cytosol of the targeted cell.

U.S. Pat. No. 4,490,362 to Shionoya, et al. teaches use of the B chain of ricin as a generalized immunopotentiator to increase immune response to infectious diseases. That reference does not suggest use of the B chain alone as a vaccine against ricin toxin.

Compositions containing either the A chain of ricin or the B chain of ricin are available commercially. Recombinant A chain has been made by recombinant methods. (See, for example, U.S. Pat. No. 4,689,401 to Ferris, which is incorporated herein by reference in its entirety.) The use of the A chain in medicinal science wherein the A chain is coupled with a targeting moiety to target to particular cells as a means of selectively destroying malignant cells is known. The ricin A chain has, in some instances, been modified when used in a conjugate for purposes of selective destruction. See, for example, U.S. Pat. No. 4,80,457 to Jansen and Gros and U.S. Pat. No. 4,962,188 to Frankel.

Goat anti-ricin polyclonal antibodies were shown to neutralize antigen at a 1:1 ratio. The goat anti-ricin antibodies fix complement and are capable of causing immunoprecipitation. However, neutralization of antigen by goat antibodies did not provide the protection to living cells that was found to be available from antibodies of the instant invention. A monoclonal antibody which is neutralizing against the ricin-B has been developed by Colombatti, et al. (*J. Immunol.* 138: 3339 (1987)) Monoclonal antibodies against the ricin-B chain were developed in association with studies related to use of $RCA_{60}$, which contains both A and B chains of ricin, for treatment of cancer. (Vetetta, E. S., *J. Immunol.* 136: 1880 (1986))

Monoclonal antibodies have been used as probes for studying the mechanism of toxicity of ricin. (Youle, et al., *J. Biol. Chem.* (1987)) However, no antibody for use in providing passive protection against ricin A is disclosed therein. Ricin A chain is being tested as a reagent for use as a toxic agent for treatment of malignancies. It is now necessary to find monoclonal antibodies which have particular value for providing passive protection against toxic effects of the A chain of ricin.

Repeated testing has shown that monoclonal antibodies to ricin which effectively bind the toxin in binding studies lack protective characteristics that are required to protect mammals who have been exposed to ricin toxin from morbidity.

DETAILED DESCRIPTION OF THE INVENTION

This invention relates to a monoclonal antibody which has proven to be particularly effective against the deleterious effects of ricin toxin. The antibodies against ricin A chain have been designated UNIVAX 70/138. Two antibodies UNIVAX 70 and 138 were generated from the same spleen and in testing were found to have the same effect. The antibody is available to the Commissioner of Patents and Trademarks upon request and will be made available to the public upon issuance of any patent claiming the antibody. The monoclonal antibodies of the invention, unlike other antibodies tested, were found to be effective in protecting mammals from morbidity arising from exposure to ricin toxin. The neutralizing action of the antibodies UNIVAX 70 and 138 does not appear to be mediated by complement or by immunoprecipitation. The antibodies of the invention are characterized as of isotype IgGl having the binding characteristics which include: a) binding specifically to the neutralizing epitope of the ricin A chain and b) providing in vitro protection of at least 95% of EL-4 cells from 100 ηg/mL ricin challenge when said antibody is present in the tissue culture at a level of at least 1000 ηg/mL.

Without relying on a particular theory for patentability, it is possible that complement fixation provides a clearance route for the goat antitoxin, while the effect of the monoclonal antibodies of this invention apparently results from binding of a particular epitope. The reduction in activity achieved with UNIVAX 70/138 reduces activity by more than three orders of magnitude.

The antibodies of the invention can also be used as a reagents to study and identify ricin toxin. The monoclonal antibody cay be labelled with enzymes such as alkaline phosphatase are used in affinity testing.

UNIVAX antibodies 70 and 138 is are isotype IgGl antibodies which is specific for ricin A chain. It is protective both in tissue culture and in in vivo studies. The antibody protected against intravenously given ricin at greater than 30×LD. furthermore, the immune response was increased in the presence of the monoclonal.

The method providing prophylactic protection afforded by the monoclonal antibodies designated UNIVAX 70 and 138 has not previously been disclosed. Furthermore, the use of a monoclonal antibody to enhance immune response with either an antigen or haptens conjugated to an antigen is novel.

A diagnostic assay for detecting the presence of ricin A chain in a proteinaceous sample comprises the steps of:
  (a) immobilizing a proteinaceous sample on a solid support;
  (b) contacting the sample with a composition containing the monoclonal antibodies of the invention;
  (c) inspecting the support to determine whether or not there is binding of the antibody to the proteinaceous material on said support.

A pharmaceutical composition comprising a prophylaxis-effective amount of an antibody which binds to the A chain of the ricin to prevent the harmful effects of ricin toxin, said antibody being administered in a pharmaceutically acceptable carrier, is also an aspect of the invention. The monoclonal antibody is an isotype IgG1 monoclonal antibody. The preferred antibodies are the UNIVAX 70 and 138 antibodies.

The antibodies for administration were grown from hybridoma and purified with protein G by usual methods. However, equivalent means known in the art may be used to purify the monoclonal antibody.

The use of toxins attached to tumor-specific antibodies is being used increasingly as a means of destroying malignant cells. The ricin toxins are being tested. The ricin A chain alone is being tested for use to destroy malignant cells. The availability of the inventive antibody to use as an anti-toxin to ameliorate untoward effects of ricin which has been administered as a therapeutic agent to a patient suffering from malignancy is an important aspect of the invention.

When administered to mammals in conjunction with antigens from the ricin toxin, the antibodies increase immune response of the body. Surprisingly, the stimulation of increased antibody response in mammals by the antibodies of the invention is not limited to response to ricin antigens. Administration of the antibodies of the invention increased host antibody production against non-ricin antigens and haptens when the non-ricin antigens and haptens are attached to ricin toxin.

EXAMPLE 1 in vitro NEUTRALIZATION OF TOXIN

In vitro neutralization of toxin was determined in an EL4 mouse leukemia cell assay. Cells were plated at 100,000 cells/well in RPMI with 10% FCS. A standard curve for ricin toxicity was determined with samples with increasing incremental antibody concentration using up to 30 ηg/ml tested in triplicate. The antibodies were titrated against a constant ricin concentration. Both UNIVAX 70 and UNIVAX 138 showed essentially the same inhibitory effect on the ricin. The test was run using 100 fold excess toxin for complete cell killing. A monoclonal antibody against Dengue was run as a negative control.

EXAMPLE 2 in vitro MOUSE PROTECTION ASSAY

CD-1 mice were obtained from Charles River (Cambridge, Mass.). Tests were conducted when the mice weighed 25 to 32 grams each. Toxin (obtained from Sigma) was diluted in phosphate buffered saline (PBS) and administered to the animals intravenously via tail vein at the dosage of 18 µg/kg. A composition containing antigen for administration was prepared by diluting 18 µg antigen in 10 ml PBS. Hence, an animal weighing 30 grams received 300 µL of the antigen-containing composition.

In vivo neutralization was determined by titrating passively administered antibody against a constant toxin challenge of 18 µkg (6X the $LD_{99}$).

The test was repeated by titrating the toxin against a constant 100 µg/mouse antibody composition.

EXAMPLE 3 in vitro COMPARISON OF ANTIBODIES

A stoichiometric competition was performed employing and ELISA format with ricin (10 µ/ml, 25 µl/well) as a plate antigen. The stoichiometric competition of antibodies UNIVAX 70 and 138 was studied four ways. The direct alkaline phosphatase labelling of the monoclonals was performed using the one-step glutaraldehyde method. Each phosphatase-labelled monoclonal was competed blind against a self monoclonal and the other monoclonal antibody. The two monoclonals could not be differentiated from one another in their ability to compete for the antigen. Both antibodies show in vitro neutralization at an antibody/toxin ration of 4:1. A comparison of the antibodies of the invention against the prior art neutralizing antibodies disclosed in the literature, the monoclonal (CETUS 753B12) and the goat anti-ricin polyclonal antibody was run in parallel with the antibodies of the invention. Protection against high toxin challenge (100×$ED_{99}$) and low toxin (−$ED_{50}$) was evaluated. The goat anti-ricin polyclonal antibody neutralized more toxin and performs better in protecting cells than the CETUS 753B12 monoclonal at both levels. Protective effects of the Cetus antibody was essentially absent in these studies at either levels of ricin administration even at a antibody:antigen ration of 100:1. The goat polyclonal antibody showed 60% protection at about 4:1 antibody to antigen ration and about 75% protection at 10:1 to 100:1 antibody to antigen ratios. Both the UNIVAX 70 and 138 showed about 10% protection at 4:1 antibody/antigen rations and high levels of cell-protecting activity of ≧99% at a 10:1 to 100:1 antibody/antigen ratios.

The antibodies of the invention may be administered parenterally in pharmaceutically acceptable carriers. Carriers such as saline solutions and buffered solutions such as lactated Ringer's solution and phosphate buffered solutions are examples of appropriate carriers for administration of the antibodies to provide passive protection of host tissues from deleterious effects of ricin toxin. If the amount of ricin toxin to which the mammal has been exposed is known, it is appropriate to administer the antibodies at dosages of at least 10 times the amount of toxin level. Administration of 10 to 1000 times the known or expected toxin levels is appropriate. For example, if the patient has been given ricin bound to an antibody for treatment of malignancy the amount of ricin administered is known.

When the antibodies of the invention are used to provide temporary passive immunity, such as when the individual is a large mammal such as a human who may be exposed to ricin toxin in a military action. The antibodies are more advantageously administered a soon as possible after exposure to ricin. In either case, the antibodies are administered at a dosage of about 10 to 10,000 µg to the affected mammal. The antibodies will be administered parenterally. While it is preferred, under controlled conditions, to administer the antibodies intravenously to the patient, the antibodies may be administered intramuscularly or subcutaneously by autoinjection. Hence, humans who are likely to be subjected to ricin toxins could carry a supply of the antibody with them for self-administration. One method of administering the antibodies is by autoinjectors such as those used to deliver snake anti-venom.

The UNIVAX 70 was deposited in the American Type Culture Collection in Bethesda, Md. on Feb. 23, 1996 where it was assigned the ATCC accession number HB-12054.

We claim:

1. A monoclonal antibody of isotype IgG1 having the binding characteristics of the antibody produced by the hybridoma which is deposited in the American Type Culture Collection and assigned the ATCC accession number HB-12054 said characteristics include:

a) binding specifically to the neutralizing epitope of the ricin A chain; and b) providing in vitro protection of at least 95% of EL-4 cells from 100 ng/mL ricin challenge when said antibody is present in the tissue culture at a level of at least 1000 ng/mL.

2. A monoclonal antibody of claim 1 which is produced by the hybridoma deposited in the American Type Culture Collection and assigned the ATCC number HB-12054.

3. A composition of matter comprising a ricin-binding, protective amount of an antibody of claim 1 in a pharmaceutically acceptable carrier.

4. The composition of claim 3, wherein said antibody is the antibody produced by the hybridoma deposited in the American Type Culture Collection and assigned the ATCC accession number HB-12054.

5. A method of counteracting the untoward effects of ricin by administration of a ricin-counteracting effective amount of a composition of claim 3 to a mammal in need of protection from untoward effects of a ricin toxin.

6. The method of claim 5, wherein said composition contains between 10 and 10,000 µg of antibody.

7. The method of claim 5, wherein said ricin has been administered to the mammal suffering from a malignancy.

8. The composition of claim 3, in an autoinjection device.

9. A composition of matter comprising an antibody of claim 1 on a solid support.

10. A composition of matter comprising an antibody of claim 1 in a cell culture media.

* * * * *